US006635611B2

(12) United States Patent
Dale

(10) Patent No.: US 6,635,611 B2
(45) Date of Patent: Oct. 21, 2003

(54) FLUIDIZED BED LOW DENSITY GRANULE

(75) Inventor: Douglas A. Dale, Pacifica, CA (US)

(73) Assignee: Genencor International, Inc., Palo Alto, CA (US)

(*) Notice: Subject to any disclaimer, the term of this patent is extended or adjusted under 35 U.S.C. 154(b) by 0 days.

(21) Appl. No.: 09/866,210

(22) Filed: May 25, 2001

(65) Prior Publication Data

US 2001/0031717 A1 Oct. 18, 2001

Related U.S. Application Data

(62) Division of application No. 09/462,431, filed on Jan. 7, 2000, now Pat. No. 6,310,027.

(60) Provisional application No. 60/108,417, filed on Nov. 13, 1998.

(51) Int. Cl.[7] .......................... C11D 3/386; C11D 7/42; C12N 9/98

(52) U.S. Cl. ...................... 510/392; 510/226; 510/320; 510/321; 510/349; 510/393; 510/441; 510/474; 510/530; 435/187

(58) Field of Search ................................ 510/392, 226, 510/320, 321, 323, 349, 393, 474, 441, 530; 435/187

(56) References Cited

U.S. PATENT DOCUMENTS

| | | | | |
|---|---|---|---|---|
| 4,106,991 A | | 8/1978 | Markussen et al. | |
| 4,689,297 A | | 8/1987 | Good et al. | |
| 4,740,469 A | | 4/1988 | Nishinaka et al. | |
| 4,760,025 A | | 7/1988 | Estell et al. | |
| 5,281,355 A | | 1/1994 | Tsayr et al. | |
| 5,324,649 A | | 6/1994 | Arnold et al. | |
| 5,342,646 A | * | 8/1994 | Kleese et al. | 427/2.1 |
| 5,733,763 A | * | 3/1998 | Markussen et al. | 435/175 |
| 5,814,501 A | | 9/1998 | Becker et al. | |
| 5,846,927 A | | 12/1998 | Vasudevan | |
| 5,879,920 A | | 3/1999 | Dale et al. | |
| 6,136,772 A | * | 10/2000 | De Lima et al. | 510/392 |
| 6,310,027 B1 | * | 10/2001 | Dale | 510/392 |

FOREIGN PATENT DOCUMENTS

| | | | |
|---|---|---|---|
| DE | 196 19 221 A 1 | | 11/1997 |
| EP | 0 304 332 A 2 | | 2/1989 |
| EP | 0 130 756 B1 | | 6/1991 |
| EP | 0 583 512 A1 | | 2/1994 |
| EP | 0 674 002 A1 | | 9/1995 |
| WO | WO-90/09440 A1 | * | 8/1990 |
| WO | WO 91/06637 | | 5/1991 |
| WO | WO 91/09941 | | 7/1991 |
| WO | WO 97/12958 | | 4/1997 |
| WO | WO 92/24177 | | 7/1997 |
| WO | WO 97/46658 | | 12/1997 |
| WO | WO 99/32595 | | 7/1999 |
| WO | WO 99/32612 | | 7/1999 |
| WO | WO 99/32613 | | 7/1999 |

* cited by examiner

*Primary Examiner*—Lorna M. Douyon
(74) *Attorney, Agent, or Firm*—Genencor International, Inc.

(57) ABSTRACT

Low-density enzyme-carrying granules are low dusting and/or storage-stable, and especially suitable for use in liquid detergents and cleaners, such as non-aqueous liquid laundry detergents. Preferred granules of the invention include a relatively high content of one or more low-density fillers, such as perlite or starch, to provide a desired product density. In one embodiment, the granules have a true density within a range of from about 1 to about 1.4 $g/cm^3$. The granules can be economically produced in commercial quantities using fluidized bed technology.

18 Claims, No Drawings

FLUIDIZED BED LOW DENSITY GRANULE

RELATED APPLICATIONS

This application is a divisional of U.S. Pat. application Ser. No. 09/462,431, filed Jan. 7, 2000, now U.S. Pat. No. 6,310,027 which claims the benefit of provisional application No. 60/108,417, filed on Nov.13 1998.

FIELD OF THE INVENTION

The present invention relates to enzyme granules for detergents and cleaners. More particularly, the present invention provides low-density, enzyme-carrying granules suitable for use in liquid detergents and cleaners.

BACKGROUND OF THE INVENTION

The use of proteins such as pharmaceutically important proteins, e.g., hormones, and industrially important proteins, e.g., enzymes, has been rapidly growing in recent years. Today, for example, enzymes find frequent use in the starch, dairy, and detergent industries, among others.

In the detergent industry, in particular, enzymes are often configured in a granular form, with an eye toward achieving one or more desirable storage and/or performance characteristics, depending upon the particular application at hand. In these regards, the industry has offered numerous developments in the granulation and coating of enzymes, several of which are exemplified in the following patents and publications:

U.S. Pat. No. 4,106,991 describes an improved formulation of enzyme granules by including within the composition undergoing granulation, finely divided cellulose fibers in an amount of 2–40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150–2,000 microns in its longest dimension, a uniform layer of enzyme around the core particle which amounts to 10%–35% by weight of the weight of the core particle, and a layer of macro-molecular, film-forming, water soluble or dispersible coating agent uniformly surrounding the enzyme layer wherein the combination of enzyme and coating agent is from 25–55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1–35% by weight of an enzyme and from 0.5–30% by weight of a synthetic fibrous material having an average length of from 100–500 micron and a fineness in the range of from 0.05–0.7 denier, with the balance being an extender or filler. The granular composition may further comprise a molten waxy material, such as polyethylene glycol, and optionally a colorant such as titanium dioxide.

U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

Notwithstanding such developments, there is a continuing need for enzyme granules which have additional beneficial or improved characteristics. For example, while enzyme granules for dry (e.g., powered) detergent formulations have become widely known and extensively developed (as exemplified above), few, if any, granule formulations are available which are suitable for incorporation in liquid detergents.

In some respects, formulators of enzyme granules for liquid detergents must address concerns much like those encountered with dry detergent formulations. It should be appreciated, however, that a liquid-detergent environment presents a variety of challenges of its own. Some of these considerations are discussed next.

In both liquid and dry detergent formulations, enzyme granules should be capable of providing sufficient enzyme activity in the wash. Thus, the enzyme load for each granule needs to be protected from the various harsh components of the liquid formulation (e.g., peroxygen bleaches, such as sodium perborate or sodium percarbonate, and the like).

Another concern, which is common to most all enzyme granules, relates to attrition resistance. In today's state of ever-increasing environmental concern and heightened awareness of industrial hygiene, it is important to keep enzyme dust within acceptable levels. It should be appreciated that human contact with airborne enzyme dust can cause severe allergic reactions. For these reasons, enzyme granule formulators continue their endeavors to control (reduce) the susceptibility of enzyme granules to attritional breakdown.

With particular regard to liquid detergent formulations, one problem with the use of particles (which would include enzyme granules) in liquids is that there is a tendency for such products to phase separate as dispersed insoluble solid particulate material drops from suspension and settles at the bottom of the container holding the liquid detergent product. Phase stabilizers such as thickeners or viscosity control agents can be added to such products to enhance the physical stability thereof. Such materials, however, can add cost and bulk to the product without contributing to the laundering/cleaning performance of such detergent compositions. Further, it is to be noted that the known enzyme granules are generally unsuitable for use in typical liquid detergents as such granules generally have an unacceptably high density (e.g., 1.45 g/cm$^3$, or higher) which would cause them to drop out of suspension in a relatively short period of time (i.e., much less than the typical product shelf life).

A further problem associated with particles in liquids is that it has been observed that the particles can induce visual inhomogeneities in the final product. This represents a problem, as composition aesthetics is a key element in terms of consumer acceptance.

In view of the above, the development of a low-density, enzyme-containing granule is needed in order to provide cleaning benefit for liquid detergents. The low density is desired so that the particles will stay suspended in the detergent throughout the intended lifecycle of the product. Additionally, it is desired to have the enzymes protected from the harsh detergent environment so that they remain active throughout the product lifecycle.

It is therefore an advantage of the present invention to provide low-density enzyme granules suitable for use in liquid-detergent or cleaner compositions. Preferred granules of the present invention are characterized by one or more of the following desirable features: they have a true density less than 1.4 g/cm$^3$; they exhibit sufficient enzyme activity in the wash; they have relatively low susceptibility to attritional breakdown; they tend to remain dispersed and suspended in the liquid detergent or cleaner during storage and use (e.g., for at least 3 weeks); they provide an acceptable (pleasing) visual appearance.

The production of such a granule exhibiting two or more of the above features has been especially challenging to the industry. For example, the industry is in need of enzyme granules for liquid detergents that have a low density (e.g., less than 1.4 g/cm$^3$), a low susceptibility to attritional breakdown (e.g., less than 50 mg/pad by Heubach), and retained activity in storage (e.g., greater than 50%). Moreover, an especially desirable granule would additionally disintegrate quickly in the wash liquor to release its enzyme activity. It is an advantage of the present invention to provide granules meeting such specifications.

For some applications, it is desirable to have granules which do not exceed a given size (diameter) specification (e.g., less than 700 micrometers). It is another advantage of the present invention to provide such low-density enzyme granules that are roughly spherical in shape and have a mean diameter of less than 700 micrometers.

It is still a further advantage of the present invention to provide low-density enzyme granules that can be made economically and in commercial quantities. To this end, the present invention provides such granules produced, at least primarily, by way of a fluidized-bed spray coating process.

SUMMARY OF THE INVENTION

One aspect of the present invention provides an enzyme granule for use in liquid detergents, such as a non-aqueous liquid laundry or dish detergent. In one embodiment, the granule has a multi-layered construction and comprises a plurality of components, including: one or more enzymes, one or more low-density fillers, and an outer coating surrounding the enzyme and filler.

According to one preferred embodiment, the granule has a true density of less than 1.4 g/cm$^3$ and one or both of the following characteristics: (i) a total dust figure of less than 50 mg/pad (as determined by Heubach test), and/or (ii) a retained activity in storage of at least 50% (e.g., 4 weeks at 37° C.). In one embodiment, the dust figure is less than 20 mg/pad, and the retained activity is at least 70%. In another embodiment, the dust figure is less than 10 mg/pad, and the retained activity is at least 80%.

In accordance with one embodiment, the granule further includes an inert seed or carrier particle, upon which the filler is built up (applied, deposited, layered, coated, etc.).

In one embodiment, the density of the final granule is within a range of from about 1 to about 1.35 g/cm$^3$, and preferably within a range of from about 1 to about 1.1 g/cm$^3$ (e.g., about 1.05 g/cm$^3$).

According to one embodiment, the granule has a diameter of no greater than about 700 micrometers (e.g., within a range of from about 400–700 micrometers, or 400–600 micrometers).

In one exemplary formulation, the enzyme is coated over the filler. In addition, or as an alternative, the enzyme can be contained (e.g., intermixed) within the filler.

Preferably, the filler is a porous material. For example, the filler can be selected from one or more of the following: perlite, fumed silica, starch, cellulose fibers, DE, feather particles, zeolites, flour, fragments of milled plant-derived materials.

In one embodiment, the multi-layered construction includes at least two layers formed in a fluidized-bed spray coater.

Another aspect of the present invention provides a multi-layered enzyme-carrying granule for use in liquid detergents, such as non-aqueous liquid laundry detergents. In one embodiment, the granule includes an inert seed or carrier particle (e.g., a sucrose crystal), an outer coating layer (including, for example PVA), and, between such particle and coating layer, a low-density filler and one or more enzymes. Preferably, the granule is characterized by having a low density, e.g., less than 1.4 g/cm$^3$ (e.g., 1–1.35 g/cm$^3$).

In one embodiment, the granule is further characterized by having a total dust figure of less than 50 mg/pad, and preferably less than 20 mg/pad (e.g., 10 mg/pad, or less), as determined by Heubach test. In addition, or as an alternative, the granule can be characterized by having a retained activity in storage of at least 50%, and preferably at least 60%, 70%, or 80% (e.g., 4 weeks at 37° C., in liquid detergent).

In an exemplary formulation, the filler is layered over the seed or carrier particle. The enzyme can then be layered over the filler, and/or contained (e.g., intermixed) within the filler.

The present invention additional provides methods for making such granules. Preferably, the method is carried out, at least primarily, in a fluidized bed apparatus. In one embodiment, the method includes the steps of:

a) selecting a seed or carrier particle;

b) coating such particle from step (a) with a low-density filler layer;

c) coating the filler layer with one or more enzymes; and d) applying a suitable outer coating.

In another embodiment, the method includes the steps of:

a) selecting a seed or carrier particle;

b) coating such particle from step (a) with a low-density filler containing at least one enzyme therein; and c) applying a suitable outer coating.

A further aspect of the present invention provides a low-density enzyme-carrying granule for use in liquid detergents (e.g., non-aqueous liquid detergents, such as a laundry detergent). In one preferred embodiment, the granule is comprised of a plurality of components, including: (i) an enzyme, (ii) a low-density filler, and (iii) an outer coating surrounding the enzyme and filler. Preferred granules, according to this embodiment, have a mean diameter of less than 700 micrometers (e.g., 400–600 micrometers), and a true density of less than 1.4 g/cm$^3$ (e.g., 1–1.35 g/cm$^3$).

According to one embodiment, the filler comprises at least 20%, and preferably at least 30%, of the final granule (wt/wt).

In terms of weight percent relative to the weight of the granule, one embodiment provides the filler as one of the two most abundant components of the granule. In an exemplary formulation, the filler is the most abundant component of the granule. In another exemplary formulation, the filler is the second most abundant component of the granule (e.g., second only to a seed or carrier particle).

According to one preferred embodiment, among all of the components, the filler contributes the most to the final density of the granule.

As previously mentioned, preferred granules of this embodiment have a density of less than 1.4 g/cm$^3$. In one embodiment, the density is between about 1–1.35 g/cm$^3$ (e.g., about 1.2 or 1.3 g/cm$^3$). In another embodiment, the density is between about 1–1.1 g/cm$^3$. In one particularly preferred embodiment, the density is about 1.05 g/cm$^3$.

As noted above, preferred granules of this embodiment have a mean diameter of less than 700 micrometers. In one embodiment, the mean diameter is no greater than about 600 micrometers. For example, the mean diameter can be within a range of from about 400 micrometers to about 600 micrometers (e.g., about 590 micrometers).

According to one embodiment, the enzyme is coated over the filler. In addition, or as an alternative, the enzyme can be contained (e.g., intermixed) within the filler.

Acceptable fillers include perlite, fumed silica, starch, cellulose fibers, DE, feather particles, zeolites, flour, fragments of milled plant-derived materials, and any mixture thereof. Particularly preferred fillers are porous.

In one embodiment, the granule is configured with multiple layers (i.e., the granule has a multi-layered construction). At least two of the layers, in this embodiment, are formed in a fluidized-bed spray coater.

Enzymes suitable for use herein include proteases, lipases, amylases, and/or cellulases, among others.

In another of its aspects, the present invention provides a low-density enzyme-carrying granule for use in liquid detergents (e.g., non-aqueous liquid detergents, such as liquid laundry detergents), comprising: a centrally-located seed or carrier particle; an outer coating layer; and, between the particle and the coating layer, a low-density filler (e.g., perlite or starch) and an enzyme. Preferably, the granule has a mean diameter of less than 700 micrometers, and a density of less than 1.4 g/cm$^3$.

In an exemplary formulation, the filler is layered over the particle (as in a fluidized-bed spray coater). The enzyme can be layered over the filler, and/or contained within the filler.

The present invention further provides methods of making such granules.

In one embodiment, the method includes the steps of:

a) selecting a seed or carrier particle;

b) coating such particle from step (a) with a low-density filler layer;

c) coating the filler layer with one or more enzymes; and d) applying a suitable outer coating.

In another embodiment, the method includes the steps of:

a) selecting a seed or carrier particle;

b) coating such particle from step (a) with a low-density filler containing at least one enzyme therein; and c) applying a suitable outer coating.

These and other features, aspects and advantages of the present invention will become apparent from the following detailed description, in conjunction with the appended claims.

DETAILED DESCRIPTION OF THE INVENTION

The present invention provides low-density, enzyme-carrying granules suitable for use in liquid detergents and cleaners. The granule design is based on using low-density fillers to provide a desired product density. The granules can be produced, for example, by way of fluidized bed technology.

As used herein, the term "density" refers to "true density" or "specific gravity," as opposed to "bulk density." True density can be determined, for example, by volume displacement using a liquid in which the granules do not dissolve (e.g., hexane).

Unless otherwise specified, percentages herein refer to weight percent relative to the total weight of the final granule.

Generally, in one preferred embodiment of the invention, a low-density, enzyme-carrying granule is made by first using a small-particle-size carrier or seed particle (e.g., a sucrose crystal). To this seed particle, a low-density filler (e.g., dry starch) along with a binder (e.g., cooked corn starch, and/or sucrose) is applied. Preferably, the filler is, in terms of weight percent, one of the most, if not the most, abundant components of the final granule. In one preferred embodiment, for example, the filler constitutes the majority of the particle (i.e., the filler ranks first (highest) in terms of weight percent among all of the granule components), and it contributes the most to the final particle density. In another exemplary embodiment, the filler ranks second in terms of weight percent, with the seed particle being the component that ranks first (highest). To the coated seed, a protein such as an enzyme (e.g., protease, lipase, amylase and/or cellulase) is applied, with or without a binder. Alternatively, the protein or enzyme can be contained (e.g., intermixed) with the low density build up on the carrier. An optional layer can be included after the enzyme. This layer can serve to add stability to the granule or provide optional density characteristics. This layer can contain, for example, salts, binders, fillers, antioxidants, reducing agents, etc. In one embodiment, the optional layer is comprised of the same material as the low-density filler. The optional layer amount is preferably 0–30%, more preferably, 10–20%. Finally, a protective coating (e.g., an outer, film-like layer including PVA and $TiO_2$) is applied. This provides a barrier to the harsh detergent elements as well as gives the desired aesthetic properties to the particle.

Seed or carrier particles are inert particles upon which an enzyme matrix (e.g., an admixture of one or more enzymes along with a filler and, optionally, a binder and/or a structuring agent) can be deposited (e.g., coated, layered, etc.). Suitable seed particles include inorganic salts, sugars, sugar alcohols, small organic molecules such as organic acids or salts, minerals such as clays or silicates or a combination of two or more of these. Suitable soluble ingredients for incorporation into seed particles include sodium chloride, potassium chloride, ammonium sulfate, sodium sulfate, sodium sesquicarbonate, urea, citric acid, citrate, sorbitol, mannitol, oleate, sucrose, lactose and the like. Soluble ingredients can be combined with dispersible ingredients such as talc, kaolin or bentonite. Seed particles can be fabricated by a variety of granulation techniques including: crystallization, precipitation, pan-coating, fluid-bed coating, fluid-bed agglomeration, rotary atomization, extrusion, prilling, spheronization, drum granulation and high shear agglomeration. In the granules of the present invention, if a seed particle is used, then the ratio of seed particles to granules is 1:1. Preferably, the seed particle delivers acceptable strength while not adversely affecting the density of the final granule. In one preferred embodiment, the carrier (seed) size is preferably 200–500 micrometers; more preferably, 250–355 micrometers. In another preferred embodiment, the seed size is 210–420 micrometers; more preferably 210–297 micrometers.

Acceptable fillers include starch, cellulose fibers, DE, feather particles, zeolites (such as used for molecular sieving), flour, milled plant derived fragments such as corn cobs, soy grit, corn syrup solids, among other small-particle, highly-porous materials. Other acceptable fillers include perlite and fumed silica (particularly, fumed silica that has been treated so as to be hydrophobic). Particularly preferred fillers are perlite, starch, and any mixture thereof. It has been found that perlite and starch are especially useful for making roughly spherical low-density granules having a diameter of less than 700 micrometers via a fluidized-bed spray coating process (as exemplified below). Other possible fillers include fly ash, borosilicate glass hollowspheres, fused glass hollowspheres, ceramic hollowspheres, plastic hollowspheres, hollow fibers (e.g., Dacron (DuPont)), low density forms of silicates (such as sodium aluminosilicates used as flow aids for powders), low density forms of silicon dioxide (such as those used as flow aids for powders), sawdust, and/or aerogel shards.

The filler amount is preferably 20–50%; more preferably, 30–40%. One preferred embodiment calls for the use of one or more porous materials as the filler.

Acceptable binders include sucrose, solubilized starch, PVA, PVP, MC, HPMC, PEG or other polymeric material. The binder amount is preferably 0–30%; more preferably, 15–25%.

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and PCT Application WO 91/06637, which are incorporated herein by reference, and cellulases such as Multifect L250™ and Puradax™, commercially available from Genencor International. Other enzymes that can be used in the present invention include oxidases, transferases, dehydratases, reductases, hemicellulases and isomerases. Among the places in the granule, where the enzyme can be loaded are in a layer around the seed particle, in the filler layer itself or as a layer over the filler layer, as well as any combination thereof. Other layers can be between an enzyme layer and the filler and/or seed particle.

Suitable synthetic polymers include polyethylene oxide, polyvinyl alcohol, polyvinyl pyrrolidone, polyvinyl pyridine, polyethylene glycol and polyethylene oxide/polypropylene oxide.

Suitable polymers include PVA, MC, HPMC and PEG. Suitable plasticizers useful in the present invention include polyols such as glycerol, propylene glycol, polyethylene glycol (PEG), urea, or other known plasticizers such as triethyl citrate, dibutyl or dimethyl phthalate or water. Suitable anti-agglomeration agents include fine insoluble or sparingly soluble materials such as talc, $TiO_2$, clays, amorphous silica, magnesium stearate, stearic acid and calcium carbonate.

A barrier layer can be used to slow or prevent the diffusion of substances that can adversely affect the protein or enzyme into the matrix. The barrier layer can be made up of a barrier material and can be coated over the protein core or the barrier material can be included in the protein core. Suitable barrier materials include, for example, inorganic salts or organic acids or salts.

As noted above, the granules of the present invention can comprise one or more coating layers. For example, such coating layers may be one or more intermediate coating layers or such coating layers may be one or more outside coating layers or a combination thereof. Coating layers may serve any of a number of functions in a granule composition, depending on the end use of the enzyme granule. For example, coatings may render the enzyme resistant to oxidation by bleach, bring about the desirable rates of dissolution upon introduction of the granule into an aqueous medium, or provide a barrier against ambient moisture in order to enhance the storage stability of the enzyme and reduce the possibility of microbial growth within the granule. The coating amount is preferably 5–20%; more preferable, 10–15%.

Suitable coatings include water soluble or water dispersible film-forming polymers such as polyvinyl alcohol (PVA), polyvinyl pyrrolidone (PVP), cellulose derivatives such as methylcellulose, hydroxypropyl methylcellulose, hydroxycellulose, ethylcellulose, carboxymethyl cellulose, hydroxypropyl cellulose, polyethylene glycol, polyethylene oxide, gum arabic, xanthan, carrageenan, chitosan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP-PVA copolymer and enteric co-polymers such as those sold under the tradename Eudragit® (Rhone Poulenc).

The coating layers of the present invention may further comprise one or more of the following: plasticizers, extenders, lubricants, pigments, and optionally additional enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers of the present invention include, but are not limited to, finely divided whiteners such as titanium dioxide or calcium carbonate or colored pigments and dyes or a combination thereof. Preferably such pigments are low residue pigments upon dissolution. Suitable extenders include sugars such as sucrose or starch hydrolysates such as maltodextrin and corn syrup solids, clays such as kaolin and bentonite and talc. Suitable lubricants include nonionic surfactants such as Neodol, tallow alcohols, fatty acids, fatty acid salts such as magnesium stearate and fatty acid esters.

Adjunct ingredients may be added to the enzyme granules of the present invention. Adjunct ingredients may include: metallic salts; solubilizers; activators; antioxidants; dyes; inhibitors; binders; fragrances; enzyme protecting agents/scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and long-chain fatty acid salts; builders; alkalis or inorganic electrolytes; bleaching agents; bluing agents and fluorescent dyes and whiteners; enzyme stabilizers such as betaine, peptides and caking inhibitors.

The granules described herein may be made by methods known to those skilled in the art of particle generation, including but not limited to fluid-bed coating, prilling, spray drying, drum granulation, high shear agglomeration, or combinations of these techniques. Most preferably, the granules are made by a fluidized-bed spray coating process (as exemplified below).

Preferably, the granules produced in accordance with the present invention are roughly spherical in shape and have a final particle size (mean diameter) of less than 700 micrometers. In one embodiment, the granules have a diameter of between about 300–700 micrometers; most preferably between about 400–600 micrometers.

The density of the granules can be measured by methods well known in the art, such as by volume displacement using a liquid in which the granules do not dissolve (e.g., hexane). Preferably, the granules produced according to the teachings herein have a true density of less than 1.4 g/cm$^3$; more preferably no greater than about 1.35 g/cm$^3$. In one embodiment, the granules have a density of between 1–1.4 g/cm$^3$; preferably between about 1–1.2 g/cm$^3$; and most preferably between about 1–1.1 g/cm$^3$. In a particularly preferred embodiment, the granules have a density of about 1.05 g/cm$^3$.

The granules of the present invention may be particularly useful in connection with non-aqueous, or predominantly non-aqueous, liquid detergents, e.g., as disclosed in PCT Publication No. WO 99/00471, incorporated herein by reference in its entirety. In one preferred embodiment, the granules are dispersed and suspended within such a liquid detergent. Preferably, the granules have a retained activity in storage (3 weeks, at 35° C.) in such a liquid detergent of at least 50%, and preferably at least 60%, and most preferably at least 70% (e.g., 80% or greater).

The following examples are representative and not intended to be limiting. One skilled in the art could choose other enzymes, fillers, binders, seed particles, methods and coating agents based on the teachings herein.

EXAMPLE 1

560 g of sucrose crystals sized 300–500 um were loaded into a Vector FL-1 fluid bed coater. The seeds were fluidized and an inlet air of 95 C. was applied. To these crystals, a solution containing 13 g of cooked corn starch, 576 g of sucrose and 851 g dry starch in 960 g water was applied using 50 psi atomization air. The resulting production yielded 1828 g product. 1261 g of the above was left in the coater and fluidized with an inlet air of temperature of 95 C. To these, 1257 g of a 6.7% active protease solution was applied using 50 psi atomization pressure. To the resulting product, a solution of 117 g titanium dioxide, 94 g methyl cellulose (Methocel A15), 32 g polyethylene glycol (PEG 600) and 19 g surfactant (Neodol 23–6.5) was applied. The resulting product weighed 1720 g. The product density was measured at 1.29 g/cm$^3$ using volume displacement with a mean particle size of 600 um.

EXAMPLE 2

700 g of sucrose crystals sized 300–355 um were loaded into a Vector FL-1 fluid bed coater. The seeds were fluidized and an inlet air of 95 C. was applied. To these crystals, a solution containing 22.8 g of cooked corn starch, 487.5 g of sucrose and 1,114.8 g dry starch in 1,312.5 g water was applied using 40 psi atomization air. The resulting production yielded 2,025 g product.

1,244 g of the above was left in the coater and fluidized with an inlet air of temperature of 95 C. To these, 1,347 g of a 6.2% active protease solution was applied using 50 psi atomization pressure. To the resulting product, a solution of 117 g titanium dioxide, 94 g methyl cellulose (Methocel A15), 32 g polyethylene glycol (PEG 600) and 19 g surfactant (Neodol 23–6.5) was applied. The resulting product weighed 1720 g. The product density was measured at 1.27 g/cm$^3$ using volume displacement with a mean particle size of 590 um.

EXAMPLE 3

627.3 g of sucrose crystals sized 300–355 um were loaded into a Vector FL-1 fluid bed coater. The seeds were fluidized and an inlet air of 95 C. was applied. To these crystals, a solution containing 25.4 g of cooked corn starch, 543.7 g of sucrose and 1,245.5 g dry starch in 1,487.7 g water was applied using 40 psi atomization air. The resulting production yielded 1,604 g product.

1,181 g of the above was left in the coater and fluidized with an inlet air of temperature of 95 C. To these, 1,184 g of a 7.1% active protease solution was applied using 50 psi atomization pressure. To the resulting product, a solution consisting of 89 g of sodium sulfate in 298 g water was applied using 50 psi. To the resulting product, a solution of 128 g titanium dioxide, 102 g polyvinyl alcohol (Elvanol 51–05) and 26 g surfactant (Neodol 23–6.5) in 904 g water was applied. The resulting product weighed 1680 g. The product density was measured at 1.35 g/cm$^3$ using volume displacement with a mean particle size of 500 um.

EXAMPLE 4

33.3 kg of sucrose crystals sized 300–355 um were loaded into a Deseret 60 fluid bed coater. The seeds were fluidized and an inlet air of 110 C. was applied. To these crystals, a solution containing 0.88 kg of cooked corn starch, 18.96 kg of sucrose and 43.32 kg dry starch in 51.7 kg water was applied using 50 psi atomization air. The resulting production yielded 87.4 kg product.

83.8 kg of the above was left in the coater and fluidized with an inlet air of temperature of 95C. To these, 100.6 kg of a 6.4% active protease solution was applied using 70 psi atomization pressure while increasing the inlet air temperature to 120C. To the resulting product, a solution consisting of 0.23 kg of cooked corn starch, 4.88 kg of sucrose and 11.15 kg dry starch in 13.3 kg water was applied using 50 psi atomization air and 100 C. inlet air temperature. To the resulting product, a solution of 9.75 kg titanium dioxide, 7.8 kg polyvinyl alcohol (Elvanol 51–05) and 1.95 kg surfactant (Neodol 23–6.5) in 69.14 kg water was applied. The resulting product weighed 168.0 kg. The product density was measured at 1.35 g/cm$^3$ using volume displacement with a mean particle size of 550 um.

EXAMPLE 5

649 g of sucrose crystals sized 300–420 um were loaded into a Vector FL-1 fluid bed coater. The seeds were fluidized and an inlet air of 95 C. was applied. To these crystals, a suspension containing 1,316 g of a 6.3% active protease, 800 g of 5% PVA (Elvanol 51–05) in water and 500 g perlite (Provosil 01) was applied using 40 psi atomization pressure. To the resulting product, a solution consisting of 3.0 g of cooked corn starch, 63.9 g of sucrose and 146.1 g dry starch in 175.0 g water was applied using 40 psi atomization air. To the resulting product, a solution of 128 g titanium dioxide, 102 g PVA (Elvanol 51–05) and 26 g surfactant (Neodol 23–6.5) was applied using 50 psi atomization pressure. The resulting product weighed 1740 g. The product density was measured at 1.3 g/cm$^3$ with a mean particle size-of 590 um.

EXAMPLE 6

Analysis of Granules

Stability

In terms of chemical (detergent) stability, granules of the present invention preferably exhibit no more than about 50% loss in activity over 3 weeks storage at 35° C. in detergent and cleaning agents (e.g., dish detergents, laundry detergents, and hot surface cleaning solutions). More preferably, the granules taught herein have a minimum of 70% activity remaining after 3 weeks at 35 C.°, and a minimum of 85% after 8 weeks at 20 C.°. In tests carried out in support of the present invention, the granules of Example 1 exhibited 73% and 99% activity remaining, respectively; and the granules of Example 4 exhibited 83% and 100% activity remaining, respectively.

Dust Tests

Two commonly used methods for measuring enzyme granule dust are the Heubach attrition test and the elutriation test. These tests attempt to quantify the tendency of enzyme granules to generate airborne protein aerosols which might potentiate allergic reactions among workers in detergent plants. These tests are designed to reproduce certain mechanical actions typical of handling, conveying and blending operations used to mix enzyme granules into detergents at commercial scale.

In the elutriation test, enzyme granules are placed on a glass frit within a tall glass tube, and fluidized with a constant dry air stream over a fixed time period. In the Heubach attrition test, granules are placed in a small, cylindrical steel chamber fitted with a rotating paddle and steel balls; the granules are pushed around by the paddle and balls, while a dry air stream percolates up through the chamber. In both tests, dust stripped from the particles by the air stream is captured on a glass fiber filter for subsequent weight measurement and activity determination. The elutriation test simulates the removal of surface dust be gentle pouring and fluidizing actions; the Heubach test is a more severe simulation of the crushing forces commonly encountered in industrial powder mixing, conveying, and sieving operations. Additional details of these tests can be found, for example, in "Enzymes In Detergency," ed. Jan H. van Ee, et al., Chpt. 15, pgs. 310–312 (Marcel Dekker, Inc., New York, N.Y. (1997)), and references cited therein.

Granules of the present invention preferably exhibit a dust figure of less than 50 mg/pad (total dust) as determined by Heubach attrition test. Exemplary granules that have been tested in support of the present invention exhibit a dust figure of no greater than 20 mg/pad, and most exhibit a dust figure of less than 10 mg/pad (all total dust, by Heubach attrition test).

Summary Table

| Sample | Density (g/cm$^3$) | Mean Particle Size |
|---|---|---|
| Example 1 | 1.29 | 600 |
| Example 2 | 1.27 | 590 |
| Example 3 | 1.35 | 500 |
| Example 4 | 1.35 | 550 |
| Example 5 | 1.30 | 590 |

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

It is claimed:

1. An enzyme granule for use in liquid detergents, said granule having a multi-layered construction and comprising a plurality of components, including:

(i) an inert particle, (ii) a low-density filler comprising starch perlite and sucrose, wherein a portion of the starch has been provided in a solublized form, (iii) an enzyme, and (iv) an outer coating surrounding said enzyme wherein said low-density filler is layered over the particle and comprises at least 20% of the weight of the enzyme granule and said enzyme is layered over the filler, wherein said granule has a true density of less than 1.4 g/cm$^3$ and a retained activity of at least 50% in storage in liquid detergent for 3 weeks at 35° C.

2. The granule of claim 1, wherein the retained activity in storage is at least 70%.

3. The granule of claim 1, wherein the density is within a range of from about 1 to about 1.35 g/cm$^3$.

4. The granule of claim 1 having a diameter no greater than about 700 micrometers.

5. The granule of claim 1, wherein said multi-layered construction includes at least three layers formed in a fluidized-bed spray coater.

6. The enzyme granule of claim 1, wherein said enzyme is selected from the group consisting of proteases, lipases, amylases and cellulases.

7. The enzyme granule of claim 6, wherein the protease is a subtilisin.

8. The enzyme granule of claim 1, wherein the inert particle is 200 to 500 micrometers.

9. The enzyme granule of claim 1, wherein the filler layer comprises at least 30% of the weight of the granule.

10. An enzyme granule for use in liquid detergents, said granule having a multi-layered construction comprising, (i) an inert particle selected from the group consisting of inorganic salts, sugars and sugar alcohols;

(ii) a low-density filler layered over the inert particle, wherein said filler comprises at least 20% of the weight of the granule and comprises starch, sucrose and perlite wherein a portion of the starch is provided in a solublized form;

(iii) an enzyme layered over the filler layer; and (iv) an outer coating surrounding the enzyme layer wherein said enzyme granule has a true density of less than 1.4 g/cm$^3$.

11. The enzyme granule of claim 10, wherein the enzyme is a protease.

12. The enzyme granule of claim 10, wherein the inert particle is sucrose crystals.

13. The enzyme granule of claim 10, wherein the diameter of said granule is no greater than about 700 micrometers.

14. The enzyme granule of claim 10, wherein the filler layer comprises at least 30% of the weight of the granule.

15. A method of making an enzyme granule, comprising:

a) selecting an inert particle;

b) coating the particle from step (a) in a fluidized-bed spray coater with a solution of cooked starch, sucrose and dry starch to obtain a layer of filler coated over the particle;

c) coating the filler layer in a fluidized-bed spray costar with one or more enzymes to obtain an enzyme layer over the filler layer; and d) applying a suitable outer coating wherein said filler comprises at least 20% of the weight of the enzyme granule and said enzyme granule having a true density of less than 1.4 g/$cm^3$.

16. The method according to claim 15, wherein said enzyme is selected from the group consisting of proteases, lipases, amylases and cellulases.

17. The method according to claim 15, wherein the inert particle is a sugar crystal, and the enzyme is selected from the group of proteases, amylases, lipases and cellulases.

18. The method according to claim 15, wherein the filler layer further comprises perlite.

* * * * *